US008765270B2

(12) United States Patent
Sekiguchi et al.

(10) Patent No.: US 8,765,270 B2
(45) Date of Patent: Jul. 1, 2014

(54) TRIAZINE COMPOUND AND ORGANIC LIGHT EMITTING DEVICE USING THE SAME

(75) Inventors: Takeshi Sekiguchi, Tokyo (JP); Naoki Yamada, Inagi (JP); Hironobu Iwawaki, Yokohama (JP); Tomona Yamaguchi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 189 days.

(21) Appl. No.: 13/139,226

(22) PCT Filed: Dec. 9, 2009

(86) PCT No.: PCT/JP2009/070942

§ 371 (c)(1), (2), (4) Date: Jun. 10, 2011

(87) PCT Pub. No.: WO2010/067894

PCT Pub. Date: Jun. 17, 2010

(65) Prior Publication Data

US 2011/0240983 A1 Oct. 6, 2011

(30) Foreign Application Priority Data

Dec. 12, 2008 (JP) ................................ 2008-316458

(51) Int. Cl.

| | |
|---|---|
| ***H01L 51/54*** | (2006.01) |
| ***C07D 251/24*** | (2006.01) |
| ***C07D 403/10*** | (2006.01) |
| ***C09K 11/06*** | (2006.01) |

(52) U.S. Cl.

USPC ............. 428/690; 313/504; 257/40; 428/917; 544/180

(58) Field of Classification Search

None

See application file for complete search history.

(56) References Cited

U.S. PATENT DOCUMENTS

| | | | | |
|---|---|---|---|---|
| 6,229,012 | B1 | 5/2001 | Hu et al. | |
| 6,821,643 | B1 * | 11/2004 | Hu et al. ........................ | 428/690 |
| 2008/0111473 | A1 * | 5/2008 | Kawamura et al. ........... | 313/504 |
| 2010/0127618 | A1 * | 5/2010 | Ohrui et al. ................... | 313/504 |

FOREIGN PATENT DOCUMENTS

| | | | |
|---|---|---|---|
| DE | 1131689 | B | 6/1962 |
| JP | 2002-069044 | A | 3/2002 |
| JP | 2004-002297 | A | 1/2004 |
| JP | 2004-022334 | A | 1/2004 |
| JP | 2006-176448 | A | 7/2006 |
| JP | 2006-225320 | A | 8/2006 |
| JP | 2007-137829 | A | 6/2007 |
| JP | 2008-290999 | A | 12/2008 |

OTHER PUBLICATIONS

Chemical Abstracts, 2008, vol. 149, Abstract No. 555099, The Retro-Diels-Alder Reaction Part II.

* cited by examiner

*Primary Examiner* — Andrew K Bohaty

(74) *Attorney, Agent, or Firm* — Canon U.S.A., Inc., IP Division

(57) ABSTRACT

Provided is an organic light emitting device having a long continuous driving lifetime. The organic light emitting device includes an anode, a cathode, and an organic compound layer which is sandwiched between the anode and the cathode, in which: one of the anode and the cathode is transparent or semi-transparent; and the organic compound layer contains at least one kind of triazine compound represented by the following general formula (1):

$$Ar\text{-}(\text{-}T)_n \quad (1)$$

where n represents an integer of 1 or 2; Ar represents a fused polycyclic aromatic group which has three or more rings and may have a substituent; and T represents a triazine group represented by the following general formula (2):

(2)

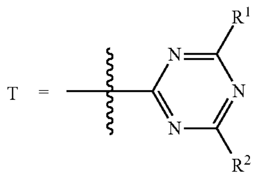

where $R^1$ and $R^2$ each represent a phenyl group or a phenyl group substituted by an alkyl group and may be identical to or different from each other.

8 Claims, 3 Drawing Sheets

TRIAZINE COMPOUND AND ORGANIC LIGHT EMITTING DEVICE USING THE SAME

TECHNICAL FIELD

The present invention relates to a triazine compound and an organic light emitting device using the same.

BACKGROUND ART

An organic light emitting device is an electronic device in which a thin film including an organic compound having a light-emitting property is provided between an anode and a cathode. Holes and electrons are injected from the respective electrodes to generate exciton of the organic compound having a light-emitting property, whereby the organic light emitting device emits light when the exciton returns to a ground state.

Recent progress of an organic light emitting device is remarkable, and the device enable a emission device with a high luminance at a low applied voltage, a variety of emission wavelengths, high-speed responsiveness, thin and light weight. From this fact, it is suggested that the organic light emitting device have a potential to find use in a wide variety of applications.

However, in the present circumstances, a more improvement in a continuous driving lifetime is needed. However, the problem has not been sufficiently solved yet.

Consequently, research and development on materials have been conducted to realize an improvement in a continuous driving lifetime, which has heretofore been one of the conventional issues. Here, there is proposed a triazine compound as a material to realize the issue of the improvement in a continuous driving lifetime. It should be noted that examples of the triazine compound and the applications of the triazine compound to an organic light emitting device include those disclosed in Japanese Patent Application Laid-Open No. 2004-022334, Japanese Patent Application Laid-Open No. 2006-225320, Japanese Patent Application Laid-Open No. 2007-137829, and U.S. Pat. No. 6,229,012.

DISCLOSURE OF THE INVENTION

The present invention has been conducted to solve the above-mentioned problem in conventional technologies. An object of the present invention is to provide a novel triazine compound useful as a constituent material of an organic light emitting device. Further, another object of the present invention is to provide an organic light emitting device having a long continuous driving lifetime.

The inventors of the present invention have studied intensively to solve the above-mentioned problem, and as a result, the inventors have completed the present invention. That is, the triazine compound of the present invention is a compound represented by the following general formula (1):

$$Ar\text{-}(\text{-}T)_n \qquad (1)$$

where n represents an integer of 1 or 2; Ar represents a fused polycyclic aromatic group which has three or more rings and may have a substituent; and T represents a triazine group represented by the following general formula (2):

(2)

T =

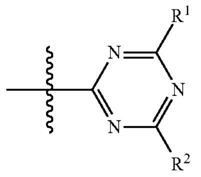

where $R^1$ and $R^2$ each represent a phenyl group or a phenyl group substituted by an alkyl group (hereinafter, referred to as "alkyl-group-substituted phenyl group) and may be identical to or different from each other; and in the general formula (1), in a case where n represents 2, multiple $R^1$'s may be identical to or different from each other and multiple $R^2$'s may be identical to or different from each other.

According to the present invention, an organic light emitting device having a long continuous driving lifetime can be provided.

Further features of the present invention will become apparent from the following description of exemplary embodiments.

BEST MODE FOR CARRYING OUT THE INVENTION

Figure 1:
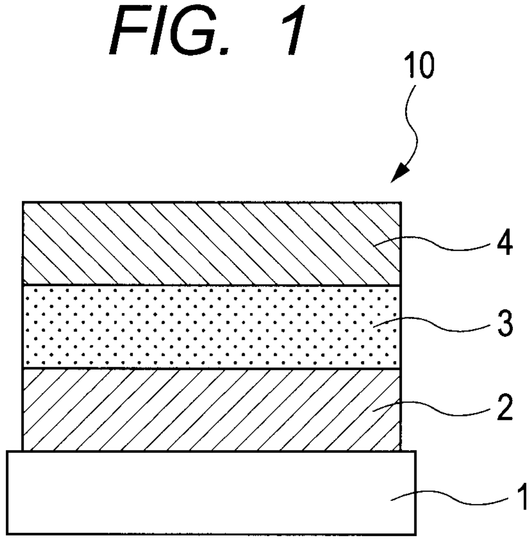
FIG. 1 is a perspective view illustrating a layer structure of a first organic light emitting device.

Hereinafter, the present invention is described in detail. First, a triazine compound of the present invention is described. The triazine compound of the present invention is a compound represented by the following general formula (1).

$$Ar\text{-}(\text{-}T)_n \qquad (1)$$

In the formula (1), n represents an integer of 1 or 2.

In the formula (1), Ar represents a fused polycyclic aromatic group having three or more rings. In the case where Ar represents a fused polycyclic aromatic group having three or more rings, an emission color can be selected from blue, green, and red by appropriately selecting the number of the fused rings and the overall structure of the fused ring. On the other hand, in the case where Ar represents a fused polycyclic aromatic group having two or less rings, the emission color of each substituent has a wavelength shorter than blue wavelengths. It should be noted that an upper limit of the number of rings of the fused polycyclic aromatic group represented by Ar is preferably 8.

Specific examples of Ar include: a fused polycyclic aromatic group having three rings such as an anthryl group and a phenanthryl group; a fused polycyclic aromatic group having four rings such as a pyrenyl group, a chrysenyl group, and a fluoranthenyl group; a fused polycyclic aromatic group having five rings such as a perylenyl group, a benzopyrenyl group, a benzofluorenyl group, and a dibenzoanthryl group; a fused polycyclic aromatic group having six rings such as an indenochrysenyl group, an indenopyrenyl group, and a dibenzofluorenyl group; a fused polycyclic aromatic group having seven rings such as a benzoindenochrysenyl group; and a fused polycyclic aromatic group having eight rings such as a diindenochrysenyl group. However, the present invention is not limited thereto.

Further, in the formula (1), Ar is a substituent which plays a role of influencing the light emitting efficiency of a device, and hence preferably has high quantum efficiency. As the substituent represented by Ar, there is preferably given a substituent derived from chrysene, benzo[k]fluoranthene, or indeno[1,2,3-hi]chrysene, which are shown below.

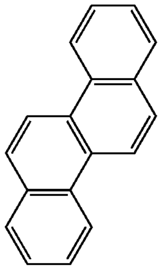

Chrysene

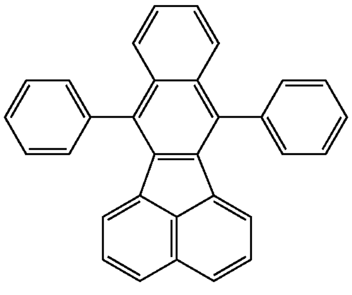

Benzo[k]fluoranthene

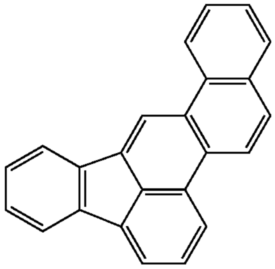

Indeno[1,2,3-hi]chrysene

Further, the fused polycyclic aromatic group represented by Ar may further have a substituent. Specific examples thereof include: an alkyl group such as a methyl group, an ethyl group, an n-propyl group, an n-butyl group, an n-pentyl group, an n-hexyl group, an n-heptyl group, an n-octyl group, an n-decyl group, an iso-propyl group, an iso-butyl group, a sec-butyl group, a tert-butyl group, an iso-pentyl group, a neopentyl group, and a trifluoromethyl group; and an aryl group such as a phenyl group, a 4-methylphenyl group, a 4-ethylphenyl group, a biphenyl group, and a naphthyl group. However, the present invention is not limited thereto.

In the formula (1), T represents a triazine group represented by the following general formula (2).

(2)

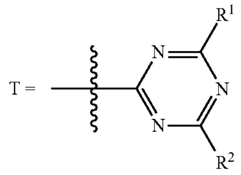

In the formula (2), $R^1$ and $R^2$ each represent a phenyl group or an alkyl-group-substituted phenyl group.

Specific examples of the alkyl-group-substituted phenyl group represented by $R^1$ and $R^2$ include a tolyl group, a dimethylphenyl group, and a mesityl group. The alkyl-group-substituted phenyl group is preferably a dimethylphenyl group or a mesityl group. When the substituents represented by $R^1$ and $R^2$ each represent a phenyl group or an alkyl-group-substituted phenyl group, concentration quenching can be more easily avoided.

It should be noted that $R^1$ and $R^2$ may be identical to or different from each other. Further, in a case where n represents 2, multiple $R^1$'s may be identical to or different from each other and multiple $R^2$'s may be identical to or different from each other.

The triazine group represented by the formula (2) has a high electron-withdrawing property and is one of the factors contributing to the continuous driving lifetime of an organic light emitting device.

The triazine compound of the present invention can be used as a constituent material of an organic light emitting device, and in particular, as a constituent material of an emission layer. When the triazine compound of the present invention is used as a constituent material of the emission layer, the continuous driving lifetime of the device is lengthened.

Hereinafter, specific structures of the triazine compound of the present invention are shown. However, those are merely representative examples, and the present invention is not limited thereto.

1

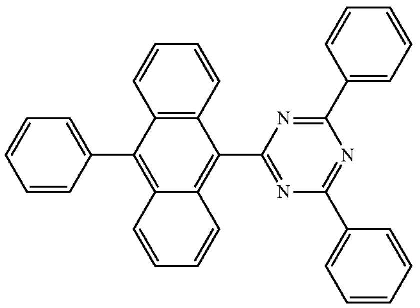

2

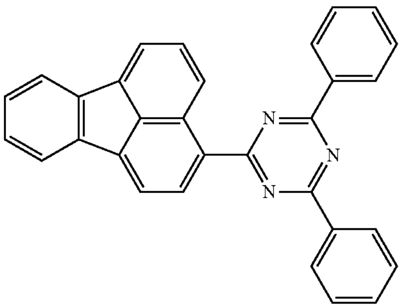

-continued
3
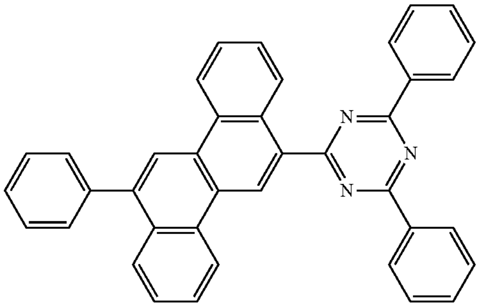
4
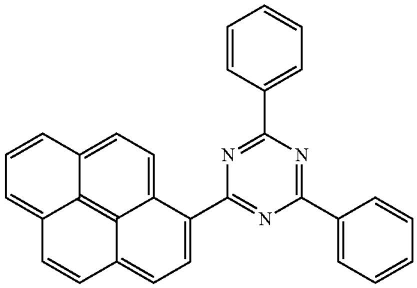
5
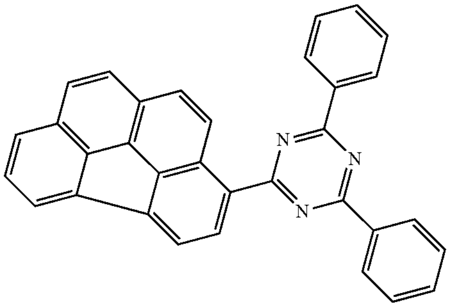
6
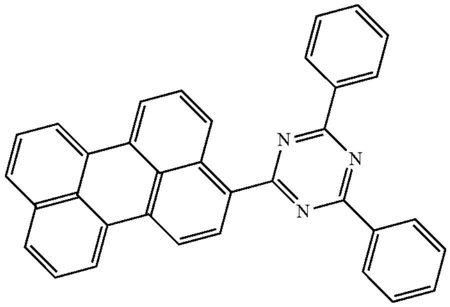
7
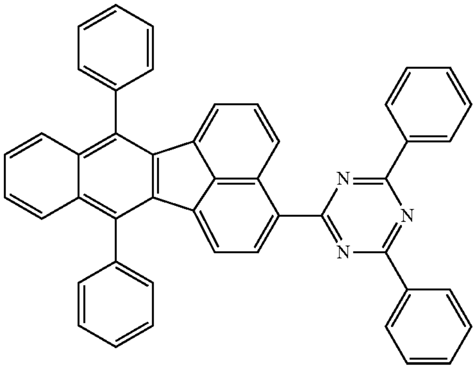
8
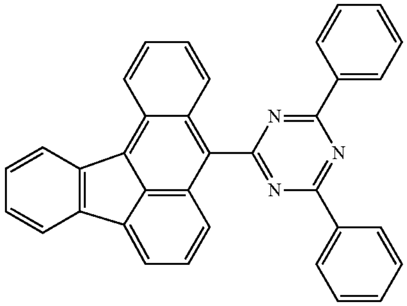
9
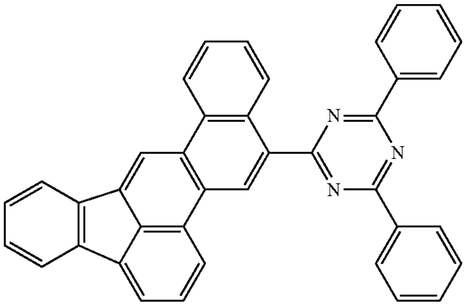
10
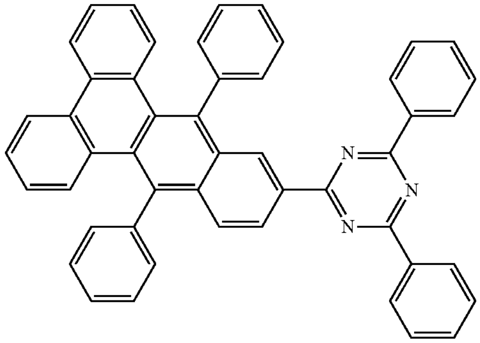

-continued
11
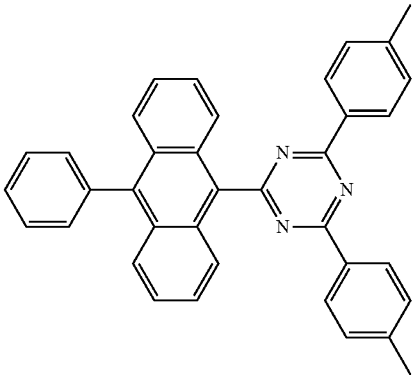
12
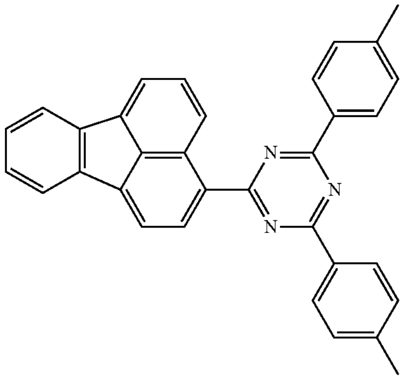
13
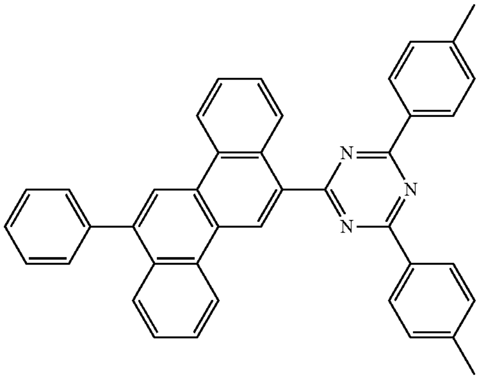
14
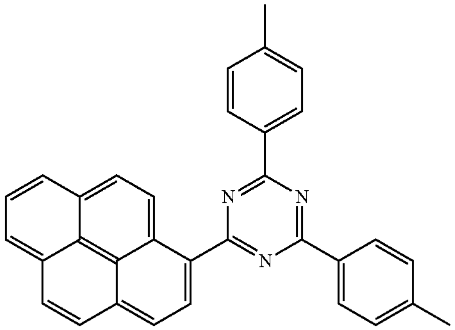
15
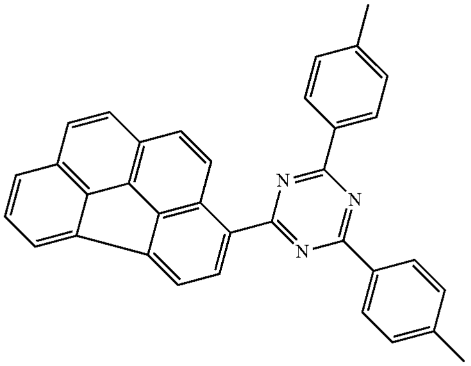
16
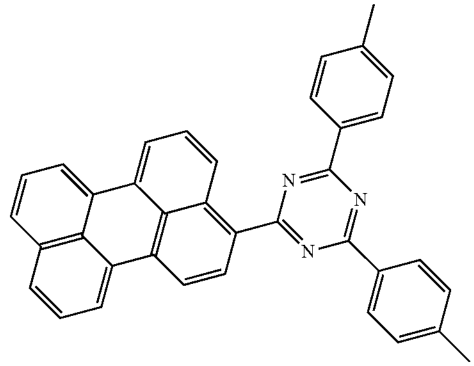
17
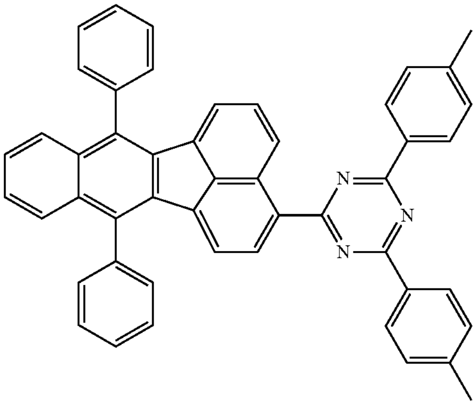
18
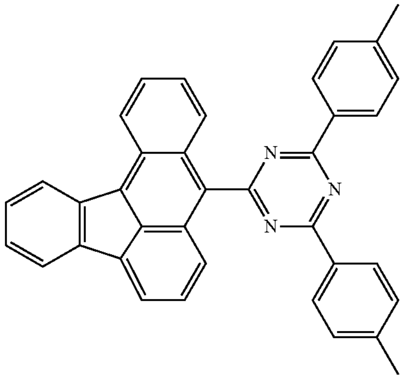

-continued
19
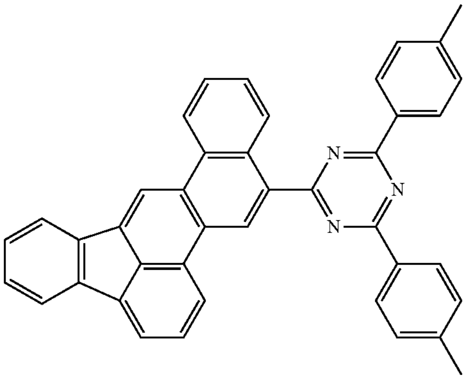
20
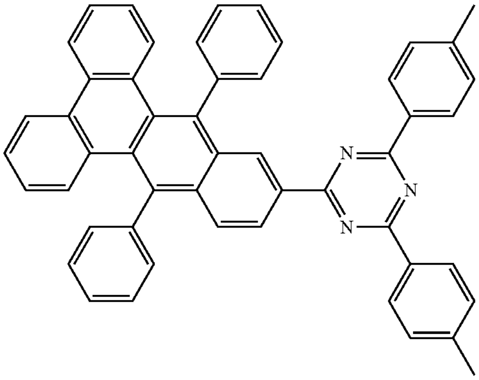
21
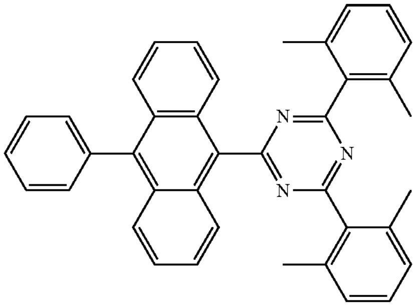
22
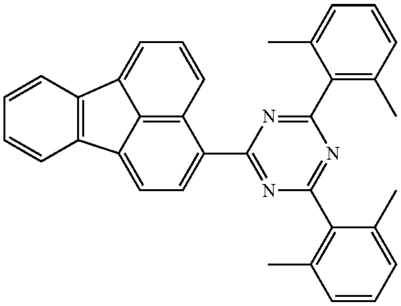
23
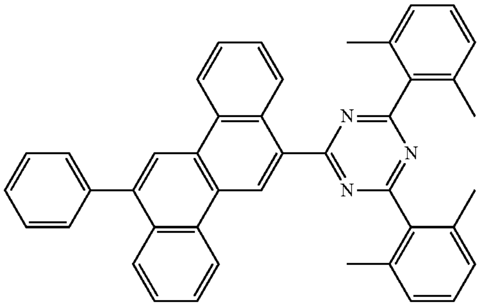
24
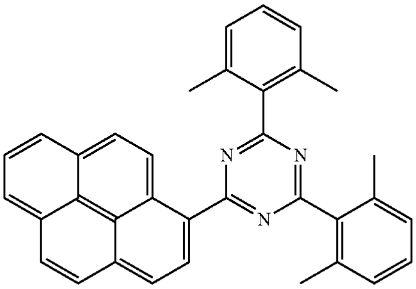
25
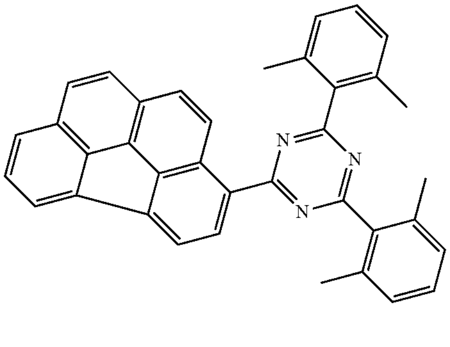
26
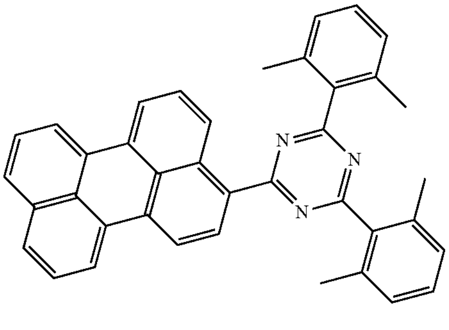

-continued
27
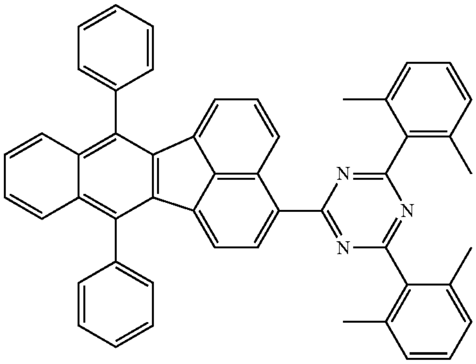
28
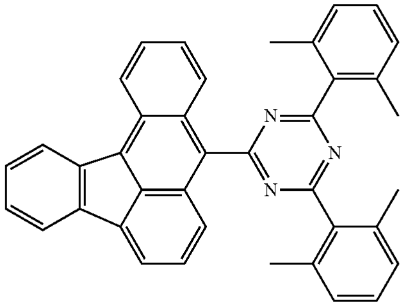
29
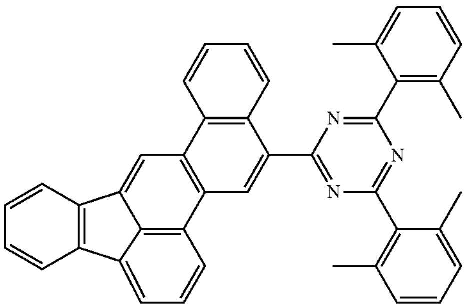
30
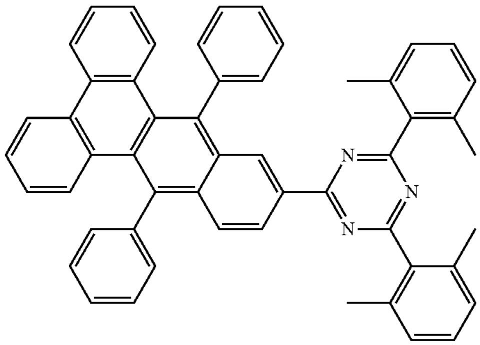
31
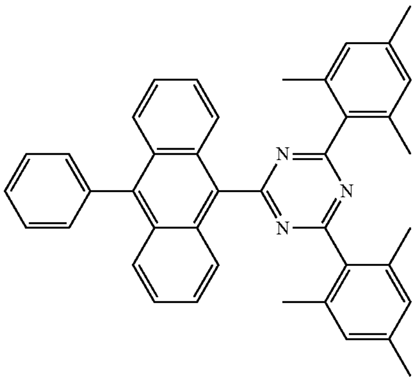
32
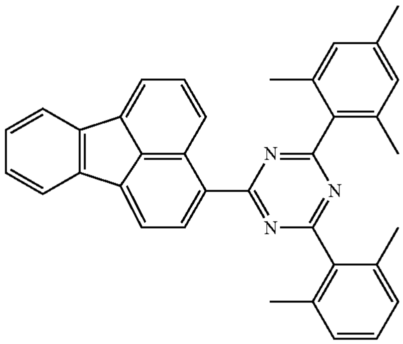
33
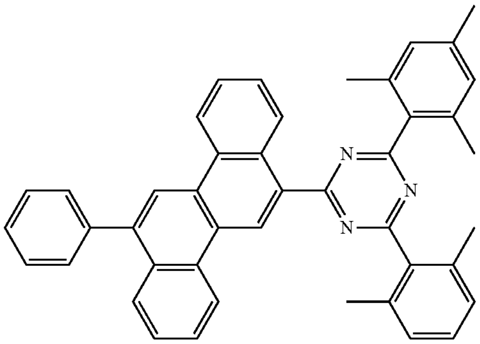
34
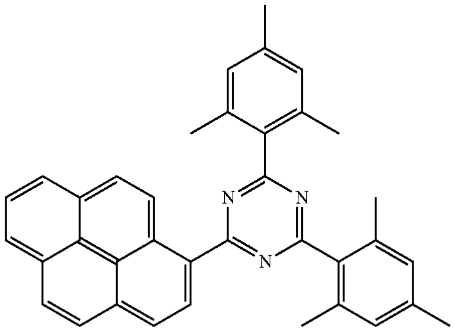

-continued
35
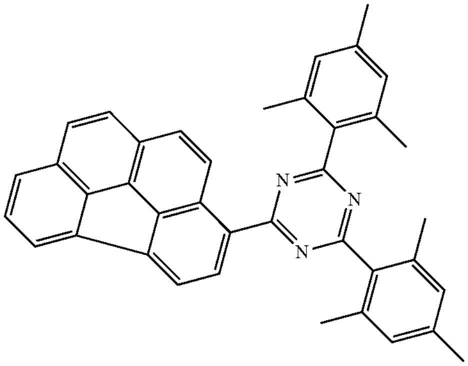
36
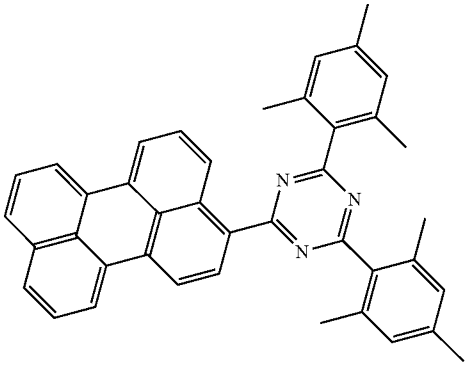
37
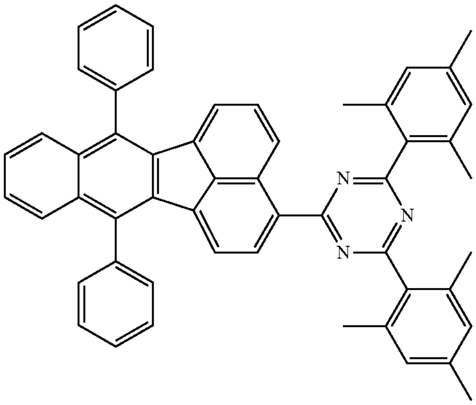
38
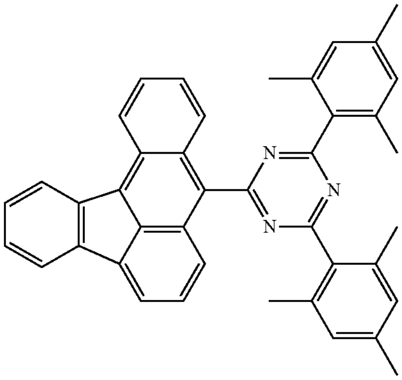
39
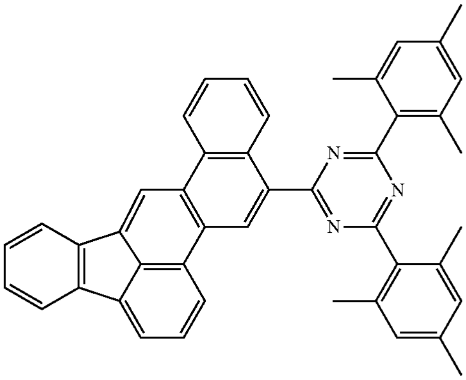
40
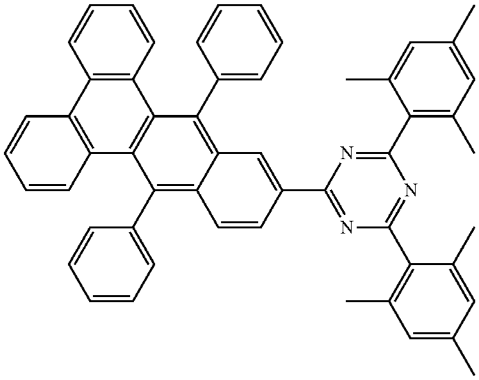
41
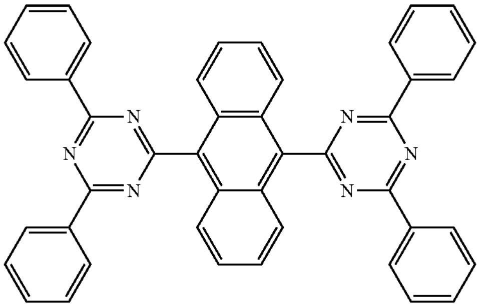
42
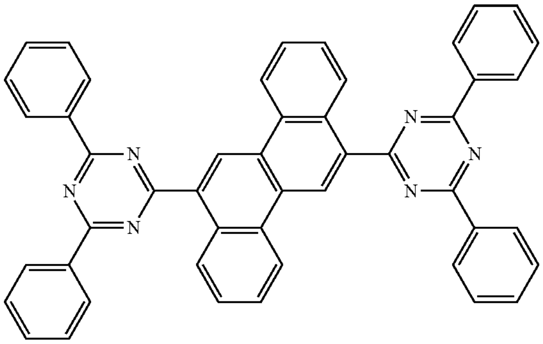

-continued
43
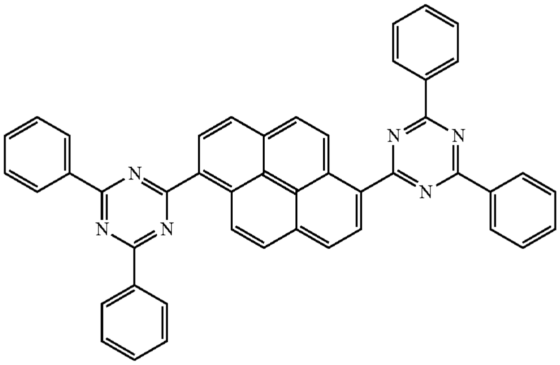
44
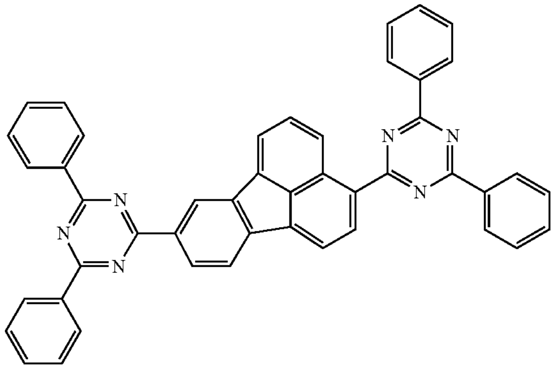
45
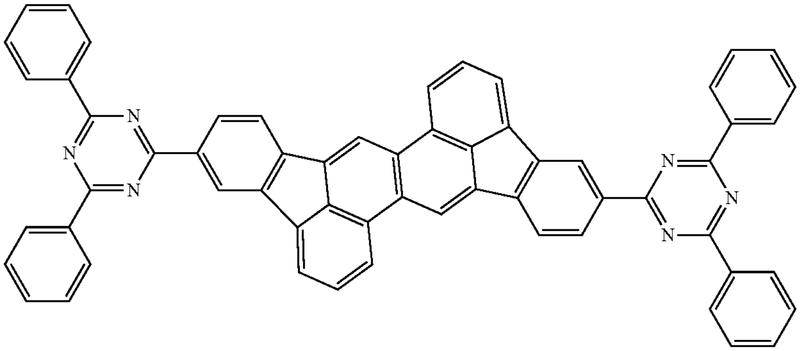
46
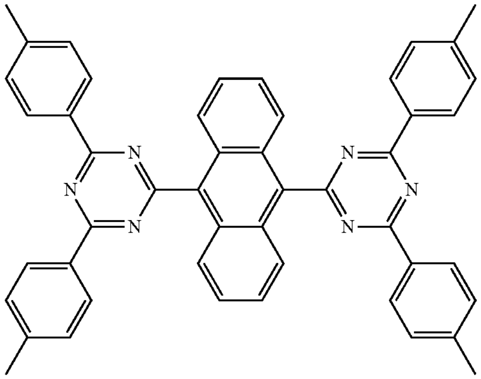
47
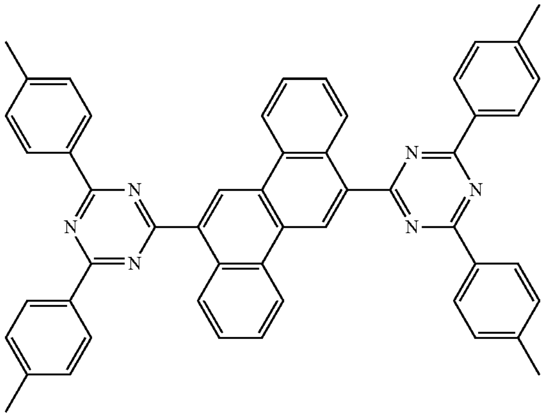
48
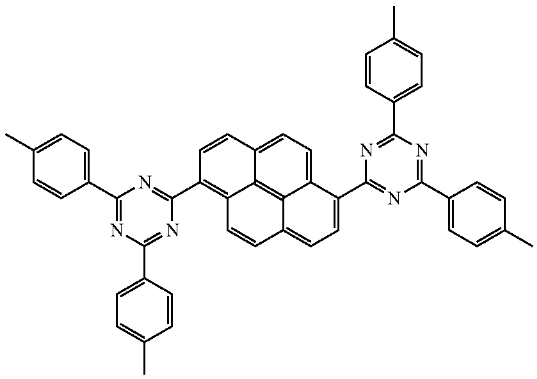
49
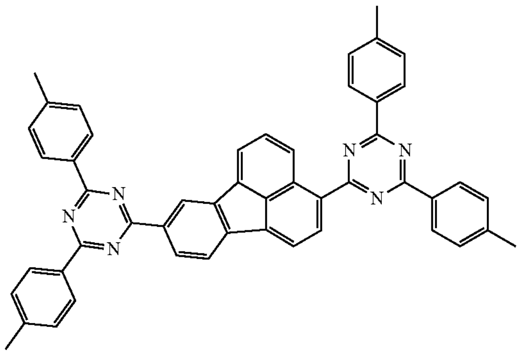

-continued
50
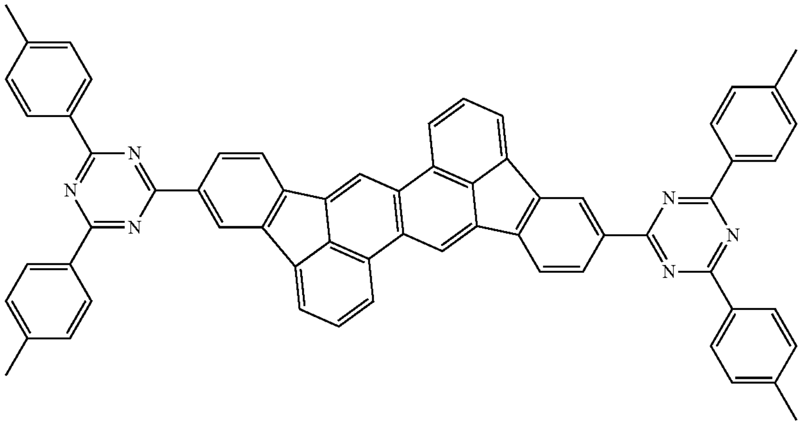
51
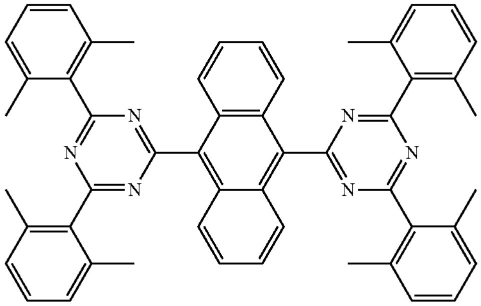
52
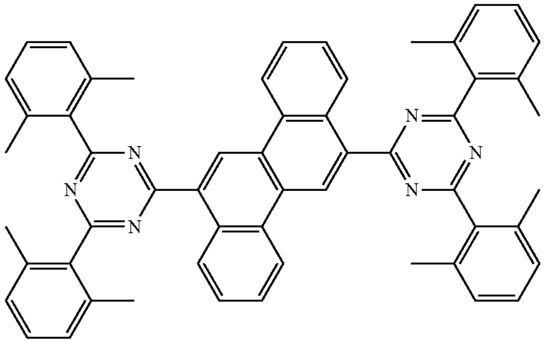
53
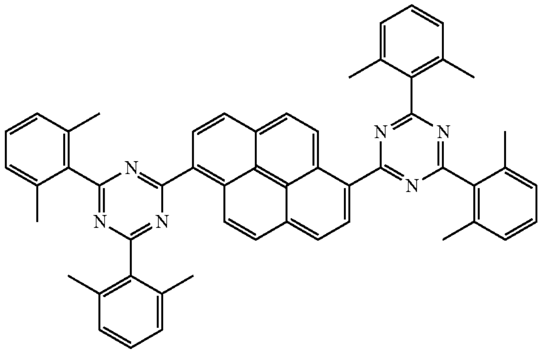
54
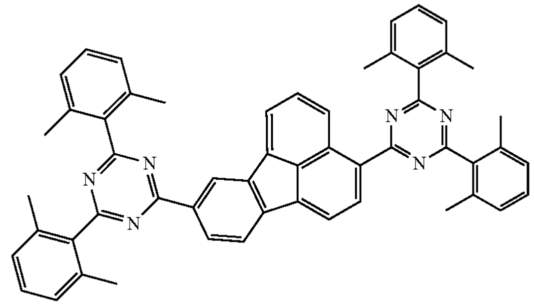
55
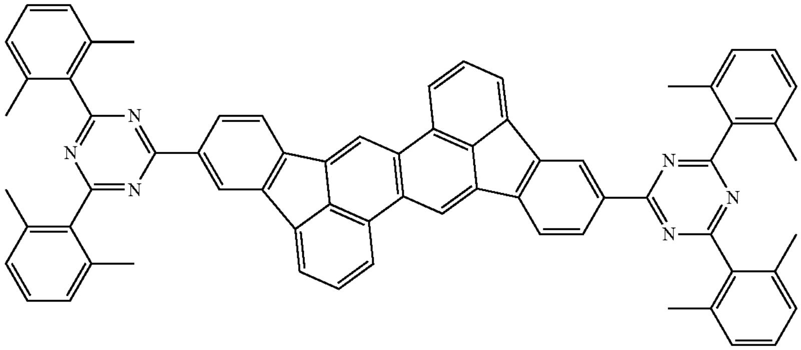

-continued
56
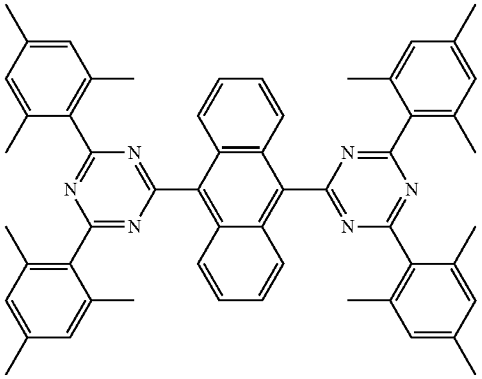
57
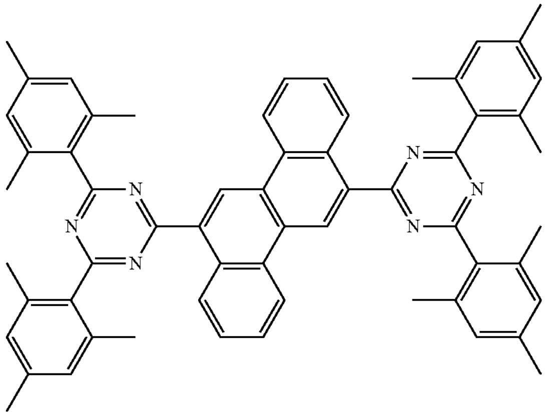
58
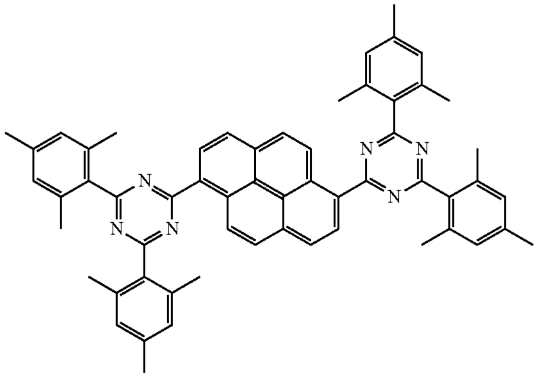
59
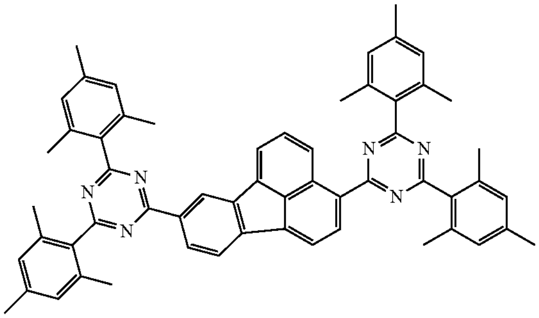
60
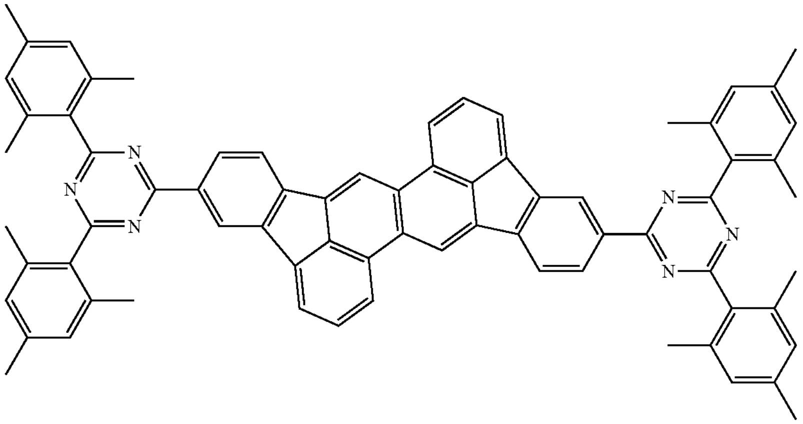
61
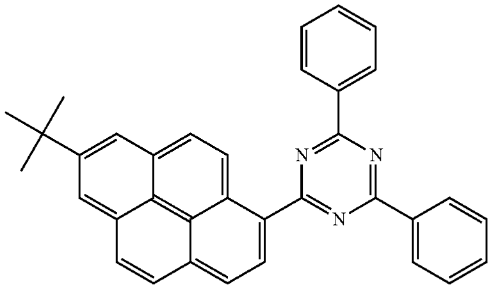
62
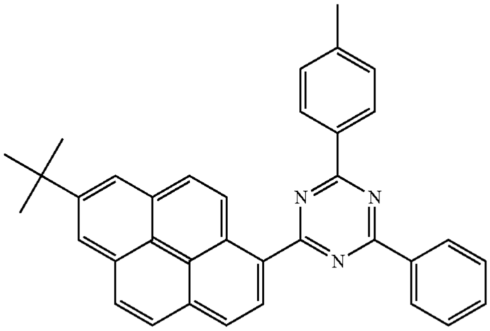

-continued

63

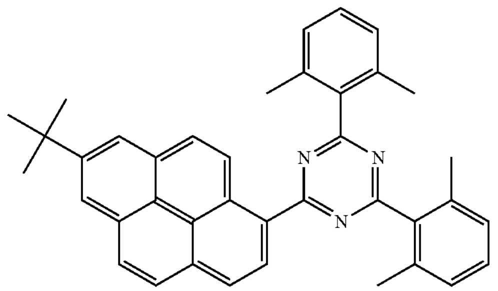

64

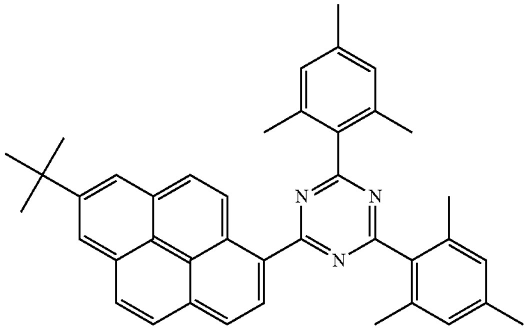

Of the above exemplified compounds, the compounds in which Ar represents a fused polycyclic aromatic group having three or four rings, i.e., the compounds belonging to Compound Group A in Table 1 below, are a group of compounds that exhibit good blue light emission.

Of the above exemplified compounds, the compounds in which Ar represents a fused polycyclic aromatic group having five to eight rings, i.e., the compounds belonging to Compound Group B in Table 1 below, are a group of compounds that exhibit good blue-green light emission.

TABLE 1

| Compound Group | Exemplified Compound | Emission color |
|---|---|---|
| A | 1 to 4, 11 to 14<br>21 to 24, 31 to 34<br>41 to 44, 46 to 49<br>51 to 54, 56 to 59<br>61 to 64 | Blue |
| B | 5 to 10, 15 to 20<br>25 to 30, 35 to 40<br>45, 50, 55, 60 | Blue-green |

Next, the organic light emitting device of the present invention is described in detail.

The organic light emitting device of the present invention includes an anode, a cathode, and an organic compound layer which is sandwiched between the anode and the cathode. Further, in the organic light emitting device of the present invention, one of the anode and the cathode is transparent or semi-transparent.

The organic compound layer may be formed of one layer or multiple layers.

In a first specific example, an organic light emitting device is formed of, in the following order, a substrate, an anode, an emission layer, and a cathode.

In a second specific example, an organic light emitting device is formed of, in the following order, a substrate, an anode, a hole transport layer, an electron transport layer, and a cathode. In this case, the hole transport layer and the electron transport layer function as an emission layer.

In a third specific example, an organic light emitting device is formed of, in the following order, a substrate, an anode, a hole transport layer, an emission layer, an electron transport layer, and a cathode.

In a fourth specific example, an organic light emitting device is formed of, in the following order, a substrate, an anode, a hole injection layer, a hole transport layer, an emission layer, an electron transport layer, and a cathode.

In a fifth specific example, an organic light emitting device is formed of, in the following order, a substrate, an anode, a hole transport layer, an emission layer, a hole/exciton blocking layer, an electron transport layer, and a cathode.

As shown in those examples, the organic compound layer placed between the anode and the cathode may be formed of various functional layers. Then, the triazine compound of the present invention is contained in at least one layer of those functional layers.

An example of the layer structure of the organic light emitting device is shown in FIG. 1. FIG. 1 shows a perspective view of the layer structure of the first organic light emitting device 10. The light emitting device 10 includes a substrate 1 such as a glass, an anode 2, an emission layer 3 and a cathode 4. The anode 2 is, for example, a reflection side electrode and itself is a reflective member or a transparent electrode having a reflective member. When the anode 2 is the reflection side electrode, the cathode 4 is a light extraction side electrode. In this case, the cathode is an electrode that is light-transmissive such as ITO.

Figure 2:
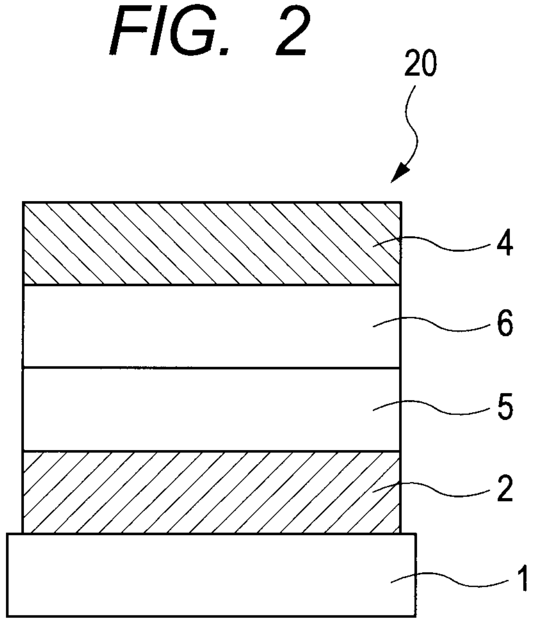
FIG. 2 is a perspective view illustrating a layer structure of a second organic light emitting device.

FIG. 2 is a perspective view illustrating a layer structure of a second organic light emitting device 20. Compared with FIG. 1, FIG. 2 shows the structure in which the emission layer 3 is not provided, and a hole transport layer 5 and an electron transport layer 6 are provided between the anode 2 and the cathode 4, stated successive order from the anode side. The structure other than the above is the same as the first strucruture. Light emission is generated from at least the hole transport layer 5 and the electron transport layer 6.

Figure 3:
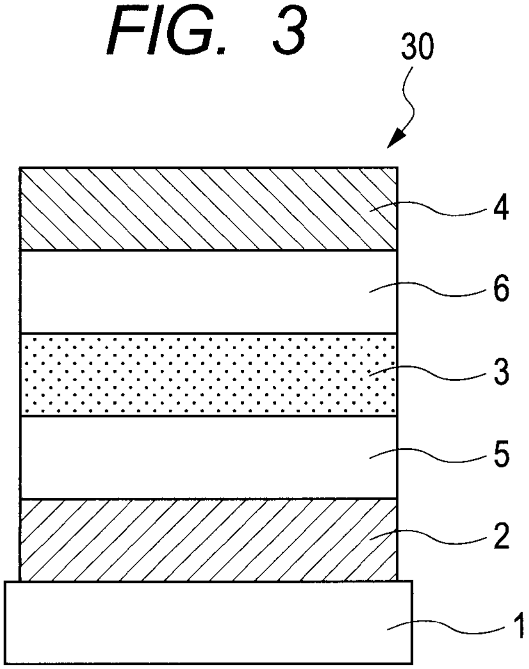
FIG. 3 is a perspective view illustrating a layer structure of a third organic light emitting device.

FIG. 3 is a perspective view illustrating a layer structure of a third organic light emitting device 30. Compared with FIG. 1, FIG. 3 shows the structure in which a hole transport layer 5 is provided between the anode 2 and the emission layer 3, and an electron transport layer 6 is provided between the emission layer 3 and the cathode 4. The structure other than the above is the same as the first strucruture.

Figure 4:
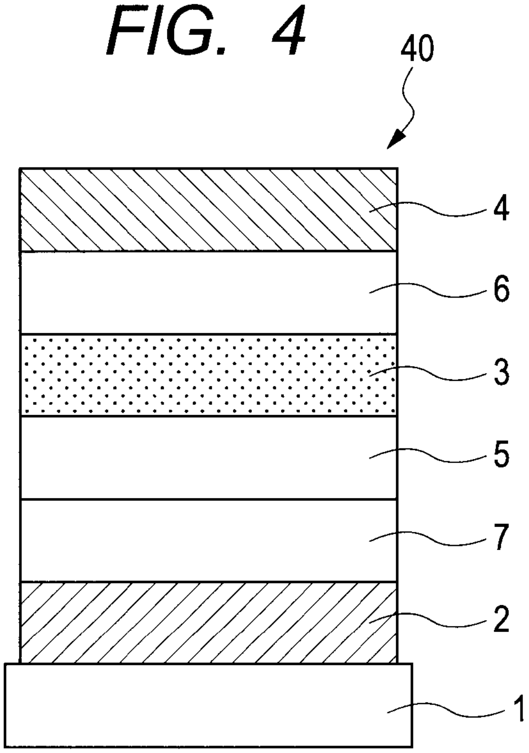
FIG. 4 is a perspective view illustrating a layer structure of a fourth organic light emitting device.

FIG. 4 is a perspective view illustrating a layer structure of a fourth organic light emitting device 40. Compared with FIG. 1, FIG. 4 shows the structure in which a hole injection layer 7 and a hole transport layer 5 are provided between the anode 2 and the emission layer 3, stated successive order from the anode side. Further, an electron transport layer 6 is provided between the emission layer 3 and the cathode 4. The structure other than the above is the same as the first strucruture.

Figure 5:
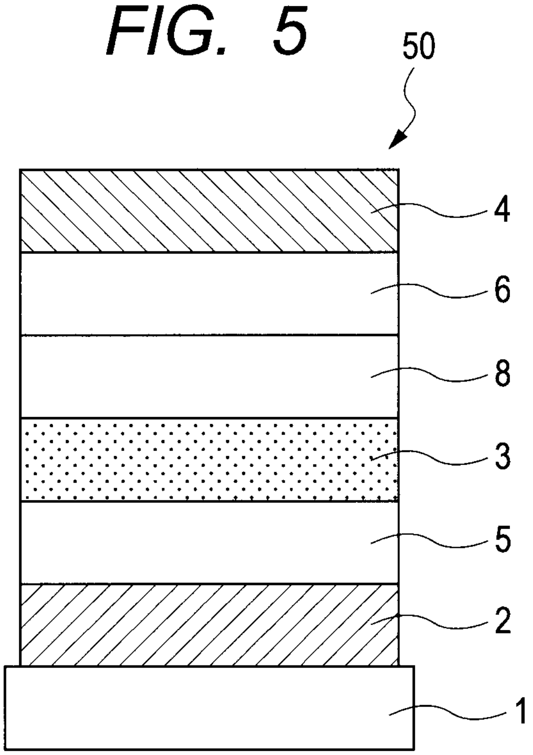
FIG. 5 is a perspective view illustrating a layer structure of a fifth organic light emitting device.

FIG. 5 is a perspective view illustrating a layer structure of a fifth organic light emitting device 50. Compared with FIG. 1, FIG. 5 shows the structure in which a hole transport layer 5 is provided between the anode 2 and the emission layer 3. Further, hole/exciton blocking layer 8 and an electron transport layer 6 are provided between the emission layer 3 and the cathode 4, stated successive order the emission layer 3 side.

The hole/exciton blocking layer serves to block hole and/or exciton. The structure other than the above is the same as the first strucruture.

The layer structure of the organic light emitting device of the present invention is not limited to those. There can be given various layer structures, for example: an insulating layer, an adhesive layer, or an interference layer is provided at an interface of an electrode and an organic layer; and a hole transport layer is formed of two layers having different ionization potentials.

In the organic light emitting device of the present invention, the organic compound layer contains at least one kind of triazine compound of the present invention. The organic compound layer used herein specifically includes, of the above functional layers, the emission layer, the hole transport layer, the electron transport layer, and the hole injection layer or the hole/exciton blocking layer. The triazine compound of the present invention is preferably contained in the emission layer, the hole transport layer, or the electron transport layer, and is more preferably contained in the emission layer. It should be noted that the triazine compound of the present invention may be contained in a single layer or may be contained in multiple layers. Further, one kind of triazine compound of the present invention or two or more kinds of triazine compounds of the present invention may be contained in one layer.

Further, the emission layer may be formed only of the triazine compound of the present invention, but is preferably formed of a host and a guest.

By the way, the chemical stability of a material for forming a device is an important factor that influences the continuous driving lifetime of an organic light emitting device.

Here, the triazine compound of the present invention is chemically stable, because the triazine compound has a reduced reactivity in terms of an electrophilic reaction of singlet oxygen molecules or the like owing to the electron-withdrawing effect derived from a triazine skeleton. Therefore, the effect of lengthening the continuous driving lifetime can be obtained by allowing the organic light emitting device to contain the triazine compound of the present invention.

When the triazine compound of the present invention is used as the host of an emission layer, the content thereof is 20 wt % to 99.9 wt % based on the total weight of a constituent material of the emission layer.

When the triazine compound of the present invention is used as the guest of an emission layer, the concentration of the guest is 0.01 wt % to 80 wt %, and preferably 1 wt % to 40 wt % based on the concentration of the host. The guest may be uniformly included throughout the emission layer and may be included with a concentration gradient. In addition, by partially incorporating the guest into a certain area, an area formed only of the host where no guest is included may be formed.

Meanwhile, irrespective of whether the triazine compound of the present invention is used as the host of the emission layer or as the guest of the emission layer, the energy gap of the host is preferably wider than that of the guest.

As described above, the organic light emitting device of the present invention is a device which uses the triazine compound of the present invention particularly as a material forming the emission layer. Moreover, in addition to the triazine compound of the present invention, a hole transporting material, a light-emitting material, an electron transporting material, or the like, which is a low-molecular material or a polymer material and is conventionally known, may be used together as required.

Those compounds are exemplified below.

A preferred hole injection/transporting material has excellent mobility to facilitate the injection of a hole from an anode and to transport the injected hole to an emission layer. As low-molecular and high-molecular materials having hole injecting transporting abilities, there are exemplified a triarylamine compound, a phenylenediamine compound, a triazole compound, an oxadiazole compound, an imidazole compound, a pyrazoline compound, a pyrazolone compound, an oxazole compound, a fluorenone compound, a hydrazone compound, a stilbene compound, a phthalocyanine compound, a porphyrin compound, and poly(vinylcarbazole), poly(silylene), poly(thiophene), and other conductive polymers, but the materials are not limited to the above.

As light-emitting materials other than the triazine compound of the present invention, the following compounds can be given. Specific examples of the compounds include, but are not limited to, polycyclic fused aromatic compounds such as a naphthalene compound, a phenanthrene compound, a fluorene compound, a pyrene compound, a tetracene compound, a coronene compound, a chrysene compound, a perylene compound, a 9,10-diphenylanthracene compound, and rubrene; a quinacridone compound; an acridone compound; a coumarin compound; a pyran compound; a Nile red; a pyrazine compound; a benzoimidazole compound; a benzothiazole compound; a benzoxazole compound; a stilbene compound; organometallic complexes including organic aluminum complexes such as tris(8-quinolinolato)aluminum, and organic beryllium complexes; and high-molecular compounds such as a poly(phenylene vinylene) compound, a poly(fluorene) compound, a poly(phenylene) compound, a poly(thienylene vinylene) compound, and a poly(acetylene) compound.

The electron injecting/transporting material may be arbitrarily selected from compounds each of which facilitates the injection of an electron from a cathode and has a function of transporting the injected electron to an emission layer. In addition, the material is selected in consideration of, for example, a balance with the carrier mobility of the hole transport material. The materials having electron injecting/transporting abilities include, but are not limited to, an oxadiazole compound, an oxazole compound, a thiazole compound, a thiadiazole compound, a pyrazine compound, a triazole compound, a triazine compound, a perylene compound, a quinoline compound, a quinoxaline compound, a fluorenone compound, an anthrone compound, a phenanthroline compound, and organometallic complexes.

Next, other members for forming the organic light emitting device of the present invention is described.

As a constituent material of an anode, a material having as large a work function as possible is preferred. Examples thereof include single metals such as gold, platinum, silver, copper, nickel, palladium, cobalt, selenium, vanadium, and tungsten, and alloys thereof; and metal oxides such as tin oxide, zinc oxide, indium oxide, indium tin oxide (ITO), and indium zinc oxide. Further, conductive polymers such as polyaniline, polypyrrole, polythiophene, and polyphenylene sulfide may also be used. Each of those electrode substances may be used singly. Alternatively, two or more of them may also be used in combination. Further, the anode may adopt any one of a single layer construction and a multilayer construction.

On the other hand, as a constituent material of a cathode, a material having a small work function is preferred. Examples thereof include: single metals such as lithium, sodium, potassium, calcium, magnesium, aluminum, indium, ruthenium, titanium, manganese, yttrium, silver, lead, tin, and chromium.

Alternatively, alloys in combination of those single metals may also be used. For example, alloys such as lithium-indium, sodium-potassium, magnesium-silver, aluminum-lithium, aluminum-magnesium, and magnesium-indium can be used. Further, metal oxides such as indium tin oxide (ITO) may also be used. Each of those electrode substances may be used singly or in combination of two or more. Further, the cathode may adopt one of a single layer construction and a multilayer construction.

Substrates used in the organic light emitting device of the present invention include: opaque substrates such as metallic substrates and ceramics substrates; and transparent substrates such as glass, quartz, and plastic sheet substrates, but are not particularly limited to those substrates. In addition, a color filter film, a fluorescent color converting film, a dielectric reflection film, or the like may be used in the substrate to control emitted light.

It should be noted that, a protective layer or a sealing layer may be formed on the prepared device to prevent the device from contacting oxygen, moisture, or the like. The protective layer may include a diamond thin film, a film made of an inorganic material such as metal oxide and metal nitride, a polymer film made of a fluorine resin, poly-para-xylene, polyethylene, a silicone resin, a polystyrene resin, and the like, or may include a photo-curable resin or the like. Further, the device itself can be covered with glass, a gas-impermeable film, a metal, or the like and packaged with an appropriate sealing resin.

The device of the present invention can also be produced by forming a thin film transistor (TFT) on a substrate and being connected thereto.

Moreover, with respect to a direction of extracting light of the device, both a bottom emission type (structure in which light is extracted from the substrate side) and a top emission type (structure in which light is extracted from a side opposite to the substrate) are acceptable.

In the organic light emitting device of the present invention, a layer containing the triazine compound of the present invention and a layer formed of another organic compound are formed by a method described below. In general, such layers are produced using a vacuum deposition method, ionization-assisted deposition method, a sputtering method, or a plasma method. In particular, a layer formed by the vacuum deposition method, a solution coating method, or the like is preferred because crystallization and the like is less likely to occur and has excellent stability with time. In addition, a thin film may be formed by dissolving the compound in a suitable solvent and subjecting the resultant to a known coating method (e.g., a spin coating method, a dipping method, a casting method, an LB method, an ink jet method, etc.). In particular, in film formation by the coating method, a film may be formed by using a compound in combination with an appropriate binder resin.

The binder resin may be selected from a wide range of binder resins. Examples thereof include, but are not limited to, a polyvinylcarbazole resin, a polycarbonate resin, a polyester resin, a polyarylate resin, a polystyrene resin, an ABS resin, a polybutadine resin, a polyurethane resin, an acrylic resin, a methacrylic resin, a butyral resin, a polyvinyl acetal resin, a polyamide resin, a polyimide resin, a polyethylene resin, a polyethersulfone resin, a diallyl phthalate resin, a phenol resin, an epoxy resin, a silicone resin, a polysulfone resin, and a urea resin. In addition, one kind of the binder resin may be used alone, or one kind or a mixture of two or more kinds may be used as a copolymer. Further, a known additive such as a plasticizer, an antioxidant, or a UV absorber, as required, may be used in combination.

Hereinafter, the present invention is described more specifically by way of examples, but the present invention is not limited thereto.

Example 1

Production Method of Exemplified Compound 7

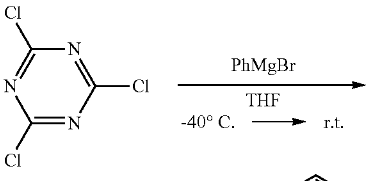

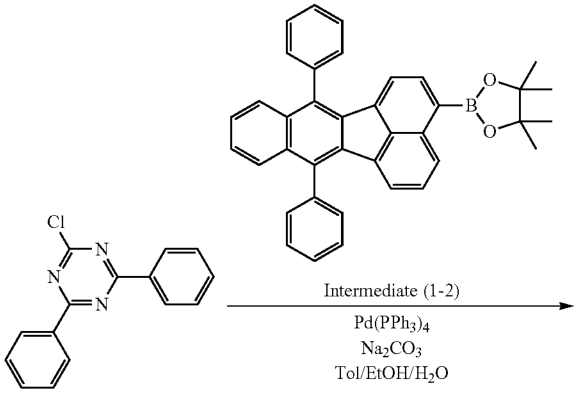

Intermediate (1-1)

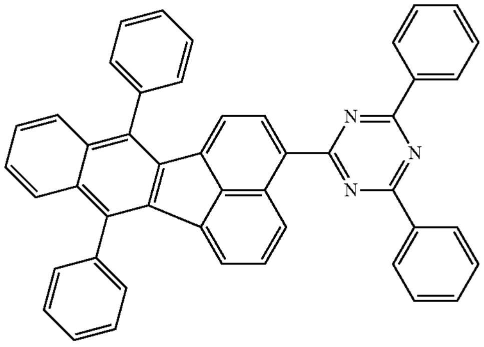

7

(1) Synthesis of Intermediate (1-1) (2-chloro-4,6-diphenyl-[1,3,5]triazine)

The following reagent and solvent were charged into a reaction container, and after that, inside of the reaction container was brought into a nitrogen atmosphere.

2,4,6-trichloro-[1,3,5]triazine: 3 g

THF: 50 mL

Next, after the reaction solution was cooled to −40° C., 16 mL of phenylmagnesium bromide (3.0 M ether solution) were dripped thereinto, and the reaction solution was stirred for 10 minutes while the liquid temperature was kept at −40° C. After that, the temperature of the reaction solution was raised to room temperature, and then the reaction solution was further stirred for 4 hours at room temperature. Next, 30 mL of water were added thereto to terminate the reaction. Then, toluene was added to the reaction solution and an organic layer was separated by a liquid separation operation. Subsequently, the organic layer was washed twice with water and dried, and after that, a crude product was obtained by removing the solvent by distillation under reduced pressure. Next, a crystal, which was produced when washing the crude product with methanol, was subjected to suction filtration, to thereby obtain 3 g of Intermediate (1-1) as a white powder.

(2) Synthesis of Exemplified Compound 7

A reaction container was brought under a nitrogen atmosphere, and after that, the following reagent and solvent were charged therein.

Intermediate (1-1): 401.3 mg (2.39 mmol)

Intermediate (1-2): 801.4 mg (1.51 mmol)

Tetrakistriphenylphosphine: 75.6 mg (0.06 mmol)

Sodium carbonate: 333.3 mg (3.14 mmol)

Toluene: 50 mL

Ethanol: 25 mL

Water: 25 mL

Next, the reaction solution was heated to 90° C. and was stirred for 5 hours at the same temperature. After the completion of the reaction, toluene and a saturated salt solution were added thereto and an organic layer was separated by a liquid separation operation. Subsequently, the organic layer was washed twice with water and dried, and after that, a crude product was obtained by removing the solvent by distillation under reduced pressure. Next, the crude product was purified by silica gel chromatography (developing solvent: toluene/heptane=1/1), and after that, the resultant was recrystallized in a toluene/ethanol mixed solvent, to thereby obtain 285 mg of Exemplified Compound 7 as a yellow powder.

Matrix-assisted laser desorption/ionization time-of-flight mass spectrometry (MALDI-TOF MS) confirmed that Compound 7 had an $M^+$ of 635.9.

The structure of the compound was identified by NMR measurement. The assignment of peaks is shown below.

$^1$H-NMR ($CDCl_3$): δ (ppm)=9.22 (1H, d, J=8.47 Hz), 8.77 (4H, d, J=6.41 Hz), 8.70 (1H, d, J=7.79 Hz), 7.72-7.56 (19H, m), 7.46-7.43 (2H, m), 6.77 (1H, d, J=7.56 Hz), 6.67 (1H, d, J=6.87 Hz).

The reduction potential was found to be −1.63 V by cyclic voltammetry (CV).

Further, the following exemplified compounds can be synthesized in the same manner as in Example 1, except that the following compounds were used instead of Intermediate (1-2) in the item (2) of Example 1.

(Exemplified Compound 1): 2-anthracene-9-yl-4,4,5,5-tetramethyl-[1,3,2]dioxaborolane (Exemplified Compound 2): 2-fluoranthene-3-yl-4,4,5,5-tetramethyl-[1,3,2]dioxaborolane (Exemplified Compound 3): 2-chrysene-6-yl-4,4,5,5-tetramethyl-[1,3,2]dioxaborolane (Exemplified Compound 4): 2-pyrene-1-yl-4,4,5,5-tetramethyl-[1,3,2]dioxaborolane (Exemplified Compound 5): 2-benzo[ghi]fluoranthene-3-yl-4,4,5,5-tetramethyl-[1,3,2]dioxaborolane Example 2

Production method of Exemplified Compound 9

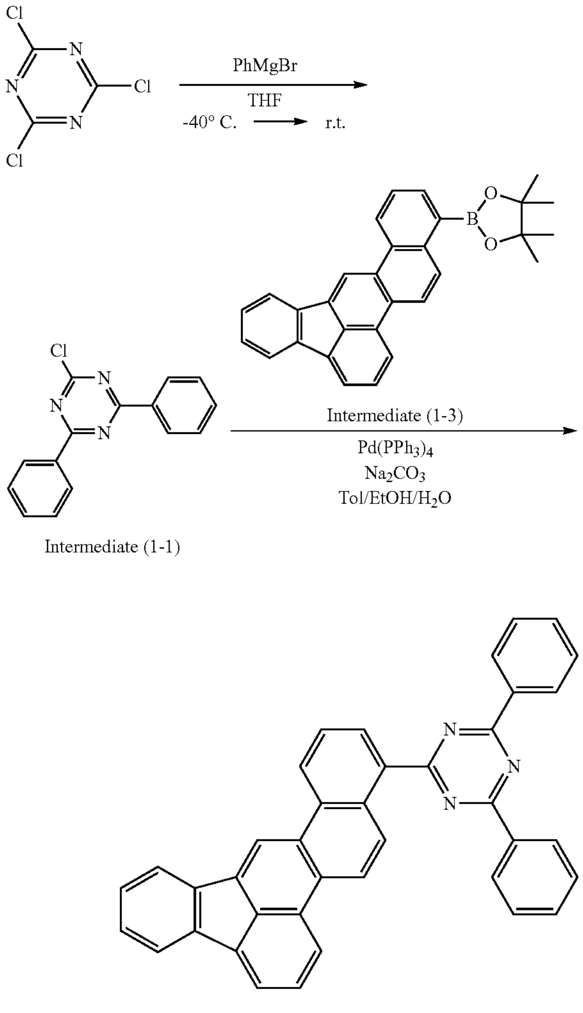

9

(1) Synthesis of Intermediate (1-1) (2-chloro-4,6-diphenyl-[1,3,5]triazine)

Intermediate (1-1) was obtained in the same manner as in Example 1 (1).

(2) Synthesis of Exemplified Compound 9

A reaction container was brought under a nitrogen atmosphere, and after that, the following reagent and solvent were charged therein.

Intermediate (1-1): 410 mg (1.52 mmol)

Intermediate (1-3): 650 mg (1.52 mmol)

Tetrakistriphenylphosphine: 180 mg (0.15 mmol)

Sodium carbonate: 1000 mg (9.43 mmol)

Toluene: 30 mL

Ethanol: 10 mL

Water: 10 mL

Next, the reaction solution was heated to 75° C. and was stirred for 3 hours at the same temperature. After the completion of the reaction, a solid, which was produced when methanol was added to the reaction solution, was subjected to suction filtration, and then the solid was washed with methanol, to thereby obtain a crude product. Subsequently, chlorobenzene was added to the crude product and washed, and after that, a solid was obtained by subjecting the resultant to suction filtration. Next, the resultant solid was purified by silica gel chromatography (developing solvent: chlorobenzene), to thereby obtain 300 mg of Exemplified Compound 9 as a yellow powder.

The structure of the compound was identified by NMR measurement. The assignment of peaks is shown below.

$^1$H-NMR ($CDCl_3$): δ (ppm)=9.65 (1H, s), 9.30 (1H, s), 9.22 (1H, d, J=8.40 Hz), 9.08 (1H, d, J=8.40 Hz), 8.85 (4H, d, J=7.20 Hz), 8.69 (1H, d, J=8.40 Hz), 8.15 (1H, dd, J=4.20 Hz, J=4.20 Hz), 7.87 (1H, d, J=7.80 Hz), 7.85 (1H, d, J=2.40 Hz), 7.78 (1H, dd, J=4.20 Hz, J=4.20 Hz), 7.66-7.60 (6H, m), 7.46 (2H, dd, J=3.30 Hz, J=3.30 Hz).

Matrix-assisted laser desorption/ionization time-of-flight mass spectrometry (MALDI-TOF MS) confirmed that Compound 9 had an $M^+$ of 533.2.

The reduction potential was found to be −1.70 V by CV.

Example 3

Production Method of Exemplified Compound 52

(1) Synthesis of Intermediate (2-1) (2-chloro-4,6-bis-[2,6-dimethyl-phenyl]-[1,3,5]triazine)

The following reagent and solvent were charged into a reaction container which was brought under a nitrogen atmosphere.

Mg: 0.8884 g

THF: 40 mL 2,6-xylylmagnesium bromide: 6.67 g

Next, the reaction solution was subjected to ultrasonic waves until the solution became completely black. After that, a mixed solution of the following reagent and solvent was dripped into the reaction solution.

2,4,6-trichloro-[1,3,5]triazine: 3 g

THF: 50 mL

Next, the reaction solution was stirred at room temperature for 1 hour. After that, the reaction solution was heated to 60° C. and was stirred for 4 hours at the same temperature, and then 30 mL of water were added thereto to terminate the reaction. Then, ethyl acetate was added to the reaction solution and an organic layer was separated by a liquid separation operation. Subsequently, the organic layer was washed twice with water and dried, and after that, a crude product was obtained by removing the solvent by distillation under reduced pressure. Next, the crude product was purified by silica gel chromatography (developing solvent: ethyl acetate/heptane=1/4), to thereby obtain 1.3 g of Intermediate (2-1) as a white powder.

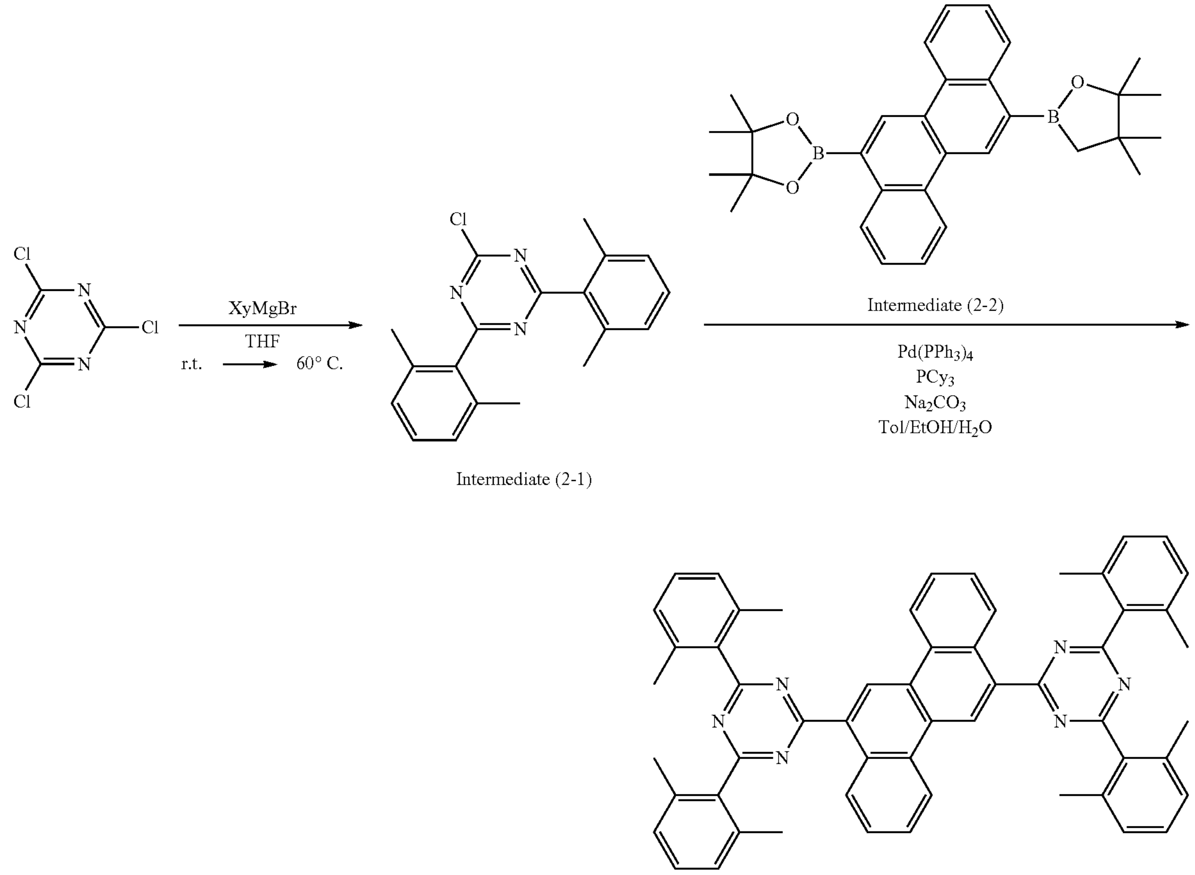

Intermediate (2-1)

52

(2) Synthesis of Exemplified Compound 52

Under a nitrogen atmosphere, the following reagent and solvent were charged into a reaction container.

Intermediate (2-1): 364 mg (0.47 mmol)
Intermediate (2-2): 230 mg (1.12 mmol)
Tetrakistriphenylphosphine: 30 mg (0.03 mmol)
Tricyclohexylphosphine: 174 mg (0.62 mmol)
Sodium carbonate: 173 mg (1.63 mmol)
Toluene: 20 mL
Ethanol: 10 mL
Water: 10 mL Next, the reaction solution was heated to 80° C. and was stirred for 2 hours at the same temperature. After that, a solid, which was precipitated when the reaction solution was left standing still and cooled to room temperature, was subjected to suction filtration, and then the solid was washed with toluene, to thereby obtain a crude product. Next, the crude product was purified by silica gel chromatography (developing solvent: chloroform/heptane=1/1), and after that, the resultant was recrystallized in toluene, to thereby obtain 179 mg of Exemplified Compound 52 as a yellow powder.

Matrix-assisted laser desorption/ionization time-of-flight mass spectrometry (MALDI-TOF MS) confirmed that Compound 52 had an $M^+$ of 802.6.

The structure of the compound was identified by NMR measurement. The assignment of peaks is shown below.

$^1$H-NMR ($CDCl_3$): δ (ppm)=9.71 (2H, s), 9.12 (2H, d, J=8.40 Hz), 8.96 (2H, d, J=8.40 Hz), 7.79 (2H, dd, J=8.40 Hz, J=8.40 Hz), 7.72 (2H, dd, J=8.40 Hz, J=8.40 Hz), 7.30 (4H, dd, J=7.60 Hz), 7.20 (8H, d, J=7.60 Hz), 2.37 (24H, s).

The reduction potential was found to be −1.56 V by CV.

Further, triazine compounds shown in Table 2 below can be synthesized in the same manner as in Example 3, except that dipinacolborolans shown in Table 2 were used instead of Intermediate (2-2) in Example 3.

TABLE 2

| Exemplified Compound | Dipinacolborolan |
|---|---|
| 51 | 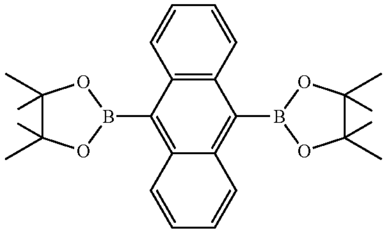 |
| 53 | 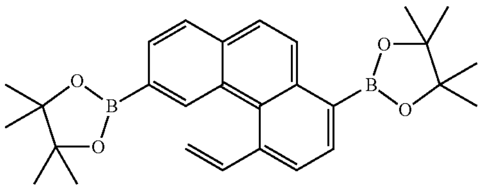 |
| 54 | 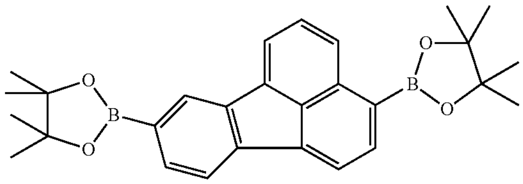 |
| 55 | 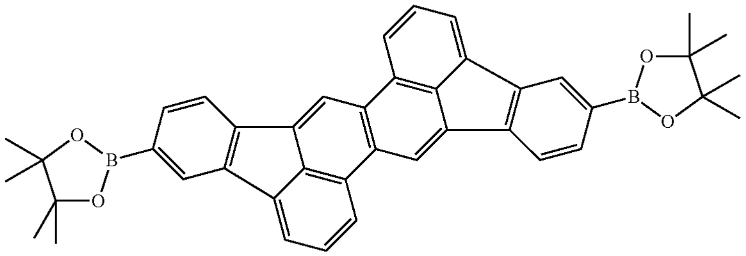 |

Example 4

An organic light emitting device having the layer structure described in the fourth layer structure was produced by a method shown below.

Indium tin oxide (ITO) was formed into a film on a glass substrate (substrate) by a sputtering method so as to serve as an anode. At this time, the thickness of the anode was 120 nm. Next, the substrate on which the ITO electrode had been formed was subjected to ultrasonic cleaning with acetone and isopropyl alcohol (IPA) in the stated order. Next, the substrate was washed with pure water, and was then dried. Further, the substrate was subjected to UV/ozone cleaning. The substrate thus treated was used as a transparent conductive supporting substrate.

Next, Compound A1 shown below was mixed with chloroform, to thereby prepare a chloroform solution at a concentration of 0.1 wt % (hereinafter, referred to as application liquid).

Compound A1

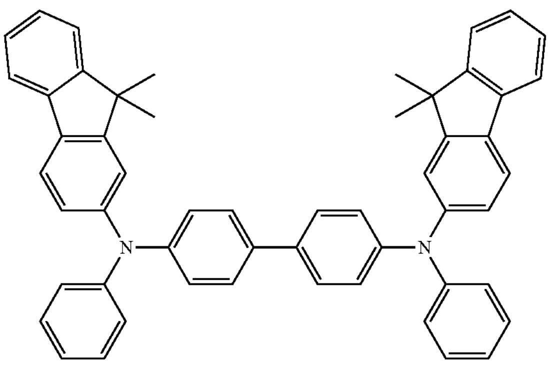

Next, the prepared application liquid was dropped onto the anode (ITO electrode), was subjected to spin coating by being rotated initially at a rotation frequency of 500 RPM for 10 seconds, and then at a rotation frequency of 1,000 RPM for 40 seconds, whereby a film was formed. After that, the thin film was dried in a vacuum oven at 80° C. for 10 minutes so that the solvent in the thin film was completely removed. As a result, the hole injection layer was formed. At this time, the thickness of the hole injection layer was about 15 nm.

Next, bis-(2,7-di-tertiary-butyl-9,9-dimetyl-9H-fluorene-4-yl)-(9,9-dimetyl-9H-fluorene-2-yl)-amine was formed into a film as a hole transport layer on the hole injection layer by a vacuum deposition method. At this time, the thickness of the hole transport layer was 15 nm, the degree of vacuum at the time of the deposition was $1.0\times10^{-4}$ Pa, and a film formation rate was 0.1 nm/sec or more to 0.2 nm/sec or less.

Next, on the hole transport layer, 7-tertiary-butyl-1-[6-(9,9-dimethyl-9H-fluorene-2-yl)-naphthalene-2-yl]-pyrene as a host and the exemplified compound as a guest were co-deposited from the vapor by a vacuum deposition method, to thereby form an emission layer. At this time, the deposition rate was adjusted in such a manner that the weight ratio of the host to the guest became 98:2. Further, the thickness of the emission layer was 30 nm, the degree of vacuum at the time of the deposition was $1.0\times10^{-4}$ Pa, and a film formation rate was 0.1 nm/sec or more to 0.2 nm/sec or less.

Next, 2,9-bis[2-(9,9'-dimethylfluorenyl)]-1,10-phenanthroline was formed into a film as an electron transport layer on the emission layer by a vacuum deposition method. At this time, the electron transport layer had a thickness of 30 nm, the degree of vacuum at the time of the deposition was $1.0\times10^{-4}$ Pa, and a film formation rate was 0.1 nm/sec or more to 0.2 nm/sec or less.

Next, lithium fluoride (LiF) was formed into a film on the electron transport layer by a vacuum deposition method, to thereby form a lithium fluoride film. At this time, the lithium fluoride film had a thickness of 0.5 nm, a degree of vacuum at the time of the deposition was $1.0\times10^{-4}$ Pa, and a film formation rate was 0.01 nm/sec. Next, aluminum was formed into a film on the lithium fluoride film by a vacuum deposition method, to thereby form an aluminum film. At this time, the aluminum film had a thickness of 120 nm, a degree of vacuum at the time of the deposition was $1.0\times10^{-4}$ Pa, and a film formation rate was 0.5 nm/sec or more to 1.0 nm/sec or less. Here, the lithium fluoride film and the aluminum film function as an electron injection electrode (cathode).

Next, the resultant organic light emitting device was covered with a protective glass plate in a dry air atmosphere lest the device should degrade owing to the adsorption of moisture, and was sealed with an acrylic resin-based adhesive. The organic light emitting device was thus obtained.

The characteristics of the obtained organic light emitting device was evaluated. To be specific, the ITO electrode (anode 2) was used as a positive electrode, the Al electrode (cathode) was used as a negative electrode, and voltage application was continued so that a current density became 100 $mA/cm^2$, and as a result, a luminance reduction rate after 300 hours was within 10%.

Example 5

An organic light emitting device was produced in the same manner as in Example 4, except that Exemplified Compound 9 was used instead of Exemplified Compound 7 as the guest of the emission layer. The characteristics of the obtained organic light emitting device was evaluated in the same manner as in Example 4. As a result, a luminance reduction rate after 300 hours was within 20%.

Example 6

An organic light emitting device was produced in the same manner as in Example 4, except that Exemplified Compound 52 was used instead of Exemplified Compound 7 as the guest of the emission layer. The characteristics of the obtained organic light emitting device was evaluated in the same manner as in Example 4. As a result, a luminance reduction rate after 300 hours was within 20%.

As described above, by using the triazine compound of the present invention as, for example, the guest of the emission layer, the organic light emitting device having a long continuous driving lifetime could be obtained.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-316458, filed Dec. 12, 2008, which is hereby incorporated by reference herein in its entirety.

The invention claimed is:

1. A triazine compound represented by the following general formula (1):

$$Ar-(-T)_n \quad (1)$$

where n represents an integer of 1 or 2;

Ar represents chrysene; and

T represents a triazine group represented by the following general formula (2):

(2)

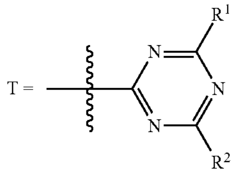

where $R^1$ and $R^2$ each represent a phenyl group or a phenyl group substituted by an alkyl group and may be identical to or different from each other; and in the general formula (1), in a case where n represents 2, multiple $R^1$'s may be identical to or different from each other and multiple $R^2$'s may be identical to or different from each other.

2. The triazine compound according to claim 1, having a structure according to formula 52 as follows:

52

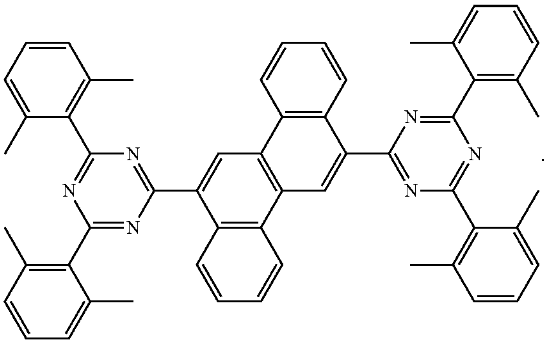

3. An organic light emitting device comprising:

an anode;

a cathode; and an organic compound layer which is sandwiched between the anode and the cathode, wherein:

one of the anode and the cathode is transparent or semi-transparent; and the organic compound layer contains at least one kind of triazine compound according to claim 1.

4. The organic light emitting device according to claim 3, wherein the triazine compound is incorporated in an emission layer.

5. The organic light emitting device according to claim 4, wherein the emission layer comprises a host and a guest.

6. The organic light emitting device according to claim 5, wherein the host is the triazine compound.

7. The organic light emitting device according to claim 5, wherein the guest is the triazine compound.

8. An apparatus comprising:

a plastic sheet substrate; and the organic light emitting device according to claim 3 which is provided on the plastic sheet substrate.

* * * * *